US009983171B2

(12) United States Patent
Jiao et al.

(10) Patent No.: US 9,983,171 B2
(45) Date of Patent: May 29, 2018

(54) AEROSPACE TRANSPARENCY HAVING MOISTURE SENSORS

(71) Applicant: PPG INDUSTRIES OHIO, INC., Cleveland, OH (US)

(72) Inventors: Yu Jiao, Blawnox, PA (US); Jeremy D. Acord, Lower Burrell, PA (US); Nicolas B. Duarte, Allison Park, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 51 days.

(21) Appl. No.: 14/810,517

(22) Filed: Jul. 28, 2015

(65) Prior Publication Data

US 2017/0030861 A1 Feb. 2, 2017

(51) Int. Cl.
*G01R 27/08* (2006.01)
*G01N 27/60* (2006.01)
*B64D 45/00* (2006.01)
*G01M 3/40* (2006.01)
*B64C 1/14* (2006.01)
(Continued)

(52) U.S. Cl.
CPC ......... *G01N 27/605* (2013.01); *B64C 1/1484* (2013.01); *B64C 1/1492* (2013.01); *B64D 15/20* (2013.01); *B64D 45/00* (2013.01); *G01M 3/40* (2013.01); *G01N 27/048* (2013.01); *G01N 27/223* (2013.01); *G01R 27/2635* (2013.01);
(Continued)

(58) Field of Classification Search
CPC ........ G01N 27/605; G01N 5/02; G01N 25/56; G01N 27/048; G01M 3/40; B64D 45/00
USPC .......................... 73/74, 75, 29.01, 29.02, 73, 73/335.01–335.14; 244/129.3; 324/664, 324/669, 694, 667, 668, 689; 340/604, 340/605; 318/483
See application file for complete search history.

(56) References Cited

U.S. PATENT DOCUMENTS 3,440,372 A  4/1969  Cecil
3,710,244 A *  1/1973  Rauchwerger ....... G01N 27/223
324/664
(Continued)

FOREIGN PATENT DOCUMENTS

JP  2007248409  9/2007
WO  WO 81/03709  12/1981
(Continued)

OTHER PUBLICATIONS

Google Search—"Coaxial Moisture Sensor" on Apr. 16, 2015.

*Primary Examiner* — Arleen M Vazquez
*Assistant Examiner* — Steven Yeninas
(74) *Attorney, Agent, or Firm* — Neil J. Friedrich (57) ABSTRACT

A transparency, e.g. an aircraft laminated windshield, includes one or more moisture sensors to monitor moisture penetration to monitor performance of the moisture barrier. At least one of the moisture sensors includes a dielectric between and in electrical contact with two electrically conductive electrodes. Alternating electrical current is applied to the electrodes to measure the complex impedance (ohms) of the dielectric to determine the amount of moisture within the laminated windshield in the area of the moisture sensor. With the information provided by the moisture sensors performance of the windshield is available to schedule timely repair or replacement of the windshield that is performing outside of acceptable limits.

20 Claims, 7 Drawing Sheets

(51) Int. Cl.
  *B64D 15/20* (2006.01)
  *G01N 27/04* (2006.01)
  *G01N 27/22* (2006.01)
  *G01R 27/26* (2006.01)

(52) U.S. Cl.
  CPC ..... *G01R 27/2641* (2013.01); *G01R 27/2647* (2013.01)

(56) References Cited

U.S. PATENT DOCUMENTS

| | | | |
|---|---|---|---|
| 4,078,107 A | 3/1978 | Bitterice et al. | |
| 4,352,059 A * | 9/1982 | Suh | G01R 27/2647 204/430 |
| 4,522,060 A | 6/1985 | Murato et al. | |
| 4,610,771 A | 9/1986 | Gillery | |
| 4,623,389 A | 11/1986 | Donley et al. | |
| 4,704,174 A | 11/1987 | Valimont et al. | |
| 4,806,220 A | 2/1989 | Finley | |
| 4,820,902 A | 4/1989 | Gillery | |
| 4,894,513 A | 1/1990 | Koontz | |
| 4,902,875 A | 2/1990 | Koontz | |
| 4,994,650 A | 2/1991 | Koontz | |
| 5,028,906 A * | 7/1991 | Moriya | G01N 27/121 338/35 |
| 5,675,944 A | 10/1997 | Kerr et al. | |
| 5,821,001 A | 10/1998 | Arbab et al. | |
| 5,959,535 A * | 9/1999 | Remsburg | A61F 13/42 128/886 |
| 6,826,948 B1 | 12/2004 | Bhatti et al. | |
| 8,155,816 B2 | 4/2012 | Rashid et al. | |
| 2005/0115308 A1 | 6/2005 | Koram et al. | |
| 2007/0002422 A1 | 1/2007 | O'Shaughnessy | |
| 2010/0163675 A1 | 7/2010 | Rashid et al. | |
| 2011/0011179 A1 | 1/2011 | Gustafsson et al. | |
| 2014/0076048 A1 * | 3/2014 | Gryska | G01N 27/223 73/335.04 |
| 2015/0137837 A1 | 5/2015 | Jiao et al. | |
| 2015/0171624 A1 | 6/2015 | Duarte et al. | |

FOREIGN PATENT DOCUMENTS

| | | |
|---|---|---|
| WO | WO 2007/009767 A2 | 1/2007 |
| WO | WO 2015/073269 A1 | 5/2015 |

* cited by examiner

AEROSPACE TRANSPARENCY HAVING MOISTURE SENSORS

BACKGROUND OF THE INVENTION

1. Field of the Invention

This invention relates to transparencies, e.g. windows, having one or more moisture sensors to measure ingress of moisture, and more particularly, to aircraft and aerospace laminated windows, e.g. laminated windshield, having moisture sensors to monitor the real time performance of moisture seals of the windshield, and the amount of moisture accumulated over time.

2. Discussion of the Presently Available Technology

Aircraft and aerospace windows, e.g. windshields include a laminate of plastic layers or sheets, glass layers or sheets and combinations thereof. The layers of an inner segment of the windshield face the interior of the aircraft and are designed to provide structural stability to the windshield. The layers of outer segment of the windshield face the exterior of the aircraft and are designed to provide structural stability and accessories for visual acuity. For example and not limiting to the discussion, one accessory to enhance visual acuity is a heatable member that includes an electrically conductive coating, or a plurality of electrically conductive wires, between and connected to a pair of spaced bus bars to heat the outer surface of the windshield to prevent the formation of, and/or to remove fog and ice on and/or from, respectively, the outer surface of the windshield.

As is appreciated by those skilled in the art, as the service time of the aircraft windshield increases, the operating efficiency of the windshield decreases until such time that the windshield becomes non-functional, and the windshield needs to be replaced or repaired. More particularly, the peripheral edge of the windshield has an outboard moisture seal that is a barrier to prevent moisture from entering between the plastic and glass layers or sheets of the windshield. When the moisture seal fails, e.g. cracks and/or the layers of the windshield laminate de-bond, moisture enters between the layers of the windshield. While the cracking or de-bonding of the seal is not a structural issue, when moisture moves between the layers of the windshield, the windshield can de-laminate, and the conductive coating or wires, whichever is present can be damaged and fall, thereby reducing or ending, the service life of the windshield. More particularly, when delamination of the windshield occurs, increased amounts of moisture move between the layers of the windshield accelerating the degradation of the windshield, e.g. damage and/or failure of the bus bars and electrically conductive coating or wires, which reduces or eliminates the defrosting capabilities of the windshield.

Untimely response to repair defects in the accessories of the transparency when they begin, decreases the operating efficiency of the transparency and can result in the need for emergency maintenance, e.g. the repair or replacement of the transparency. It would be advantageous, therefore, to provide a transparency with moisture sensors to monitor the performance of the transparency so that the repair, or replacement, of the transparency is a scheduled maintenance and not an emergency maintenance.

SUMMARY OF THE INVENTION

This invention relates to an aircraft windshield having, among other things, a plurality of sheets joined together to provide a laminated window having a vision area, the window having a moisture seal on the peripheral and marginal edge portions of the sheets. A moisture is positioned between the sheets and/or between the sheets and the moisture seal. The moisture sensor includes, among other things, a dielectric member between a first electrode and a second electrode wherein the dielectric material is in electrical contact with the first and second electrodes and maintains the first and the second electrodes spaced from one another and out of the surface contact with one another. Sensor electronics are operatively connected to the electrodes of the moisture sensor to measure an electrical property of the sensor to determine amount of moisture absorbed by the dielectric member, wherein applying alternating electrical current to the first and the second electrodes and measuring the complex impedance (ohms) of the dielectric material measures the amount of moisture within the laminated windshield in the area of the moisture sensor.

The invention further relates to a method of making an aircraft transparency having a moisture sensor. The method includes, among other things, fabricating a laminated aircraft transparency having a moisture barrier over the outer surface of the marginal edges of, and periphery of the laminated aircraft transparency. During fabrication of the laminated aircraft transparency placing a sensor element responsive to moisture between the sheets and/or between the sheets and the moisture seal of the aircraft transparency. In one non-limiting embodiment of the invention, the sensor element includes, among other things, a dielectric member between a first electrode and a second electrode wherein the dielectric material is in electrical contact with the first and second electrodes and maintains the first and the second electrodes spaced from one another and out of contact with one another, applying alternating electrical current to the electrodes to measure the complex impedance (ohms) of the dielectric to determine the amount of moisture within the laminated windshield in the area of the moisture sensor.

DETAILED DESCRIPTION OF THE INVENTION

As used herein, spatial or directional terms such as "inner", "outer", "left", "right", "up", "down", "horizontal", "vertical", and the like, relate to the invention as it is shown in the drawing on the figures. However, it is to be understood that the invention can assume various alternative orientations and, accordingly, such terms are not to be considered as limiting. Further, all numbers expressing dimensions, physical characteristics, and so forth, used in the specification and claims are to be understood as being modified in all instances by the term "about". Accordingly, unless indicated to the contrary, the numerical values set forth in the following specification and claims can vary depending upon the property desired and/or sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between and inclusive of the minimum value of 1 and the maximum value of 10; that is, all subranges beginning with a minimum value of 1 or more and ending with a maximum value of 10 or less, e.g., 1 to 6.7, or 3.2 to 8.1, or 5.5 to 10. Also, as used herein, the term "applied over", "positioned over" or "mounted over" means applied on, positioned on or mounted over but not necessarily in surface contact with. For example, one article or component of an article "applied over", "mounted over" or "positioned over" another article or component of an article does not preclude the presence of materials between the articles, or between components of the article, respectively.

Before discussing several non-limiting embodiments of the invention, it is understood that the invention is not limited in its application to the details of the particular non-limiting embodiments shown and discussed herein since the invention is capable of other embodiments. Further, the terminology used herein to discuss the invention is for the purpose of description and is not of limitation. Still further, unless indicated otherwise, in the following discussion like numbers refer to like elements.

Non-limiting embodiments of the invention are directed to an aircraft laminated transparency, and in particular to an aircraft laminated windshield. The invention, however, is not limited to any particular type of aircraft transparency, and the invention contemplates the practice of the invention on any type of windshield, e.g. but not limited to (1) a laminated windshield disclosed in U.S. Pat. No. 8,155,816; (2) an aircraft window having a medium responsive to electric stimuli to increase or decrease visible transmission, e.g. but not limited to the type of aircraft window disclosed in U.S. Published Patent application 2007/0002422A, and (3) aircraft windows of the type having an insulated air space between a pair of laminated sheets. Further, the invention can be practiced on commercial and residential windows, e.g. but not limited to (1) the type disclosed in U.S. Pat. No. 5,675,944; (2) a window for any type of land vehicle; (3) a canopy, cabin window and windshield for any type of air and space vehicle; (4) a window for any above and/or below water vessel, and (5) a window for a viewing side or door for any type of containers, for example but not limited to a refrigerator, cabinet and/or oven door. The documents identified herein are hereby incorporated by reference. Still further, the invention is not limited to the material of the layers or sheets of the transparency, and the layers or sheets can be made of, but not limited to, cured and uncured plastic sheets; annealed glass sheets, and heat and chemically strengthened, clear, colored, coated and uncoated glass sheets The laminated windshield is usually designed to be a passive component of the aircraft with de-icing and/or de-fogging features. In the practice of the non-limiting aspects of the invention, sensors are used to provide feedback on the performance of the transparency. More particularly, the moisture sensors of the invention provide an intelligent window with the goal of providing feedback on the health status of the window system for electrical and mechanical integrity. Specifically, moisture ingress is a known problem of aerospace transparency aging, especially when window seals are not properly maintained. If left to continue, moisture ingress can permanently deteriorate the interior laminate, causing reduced visibility and rendering the window useless. In the worst cases, moisture ingress can affect the electrically conductive heater layer (discussed in detail below), potentially causing arcing and structure failure of one or more layers, sheets or plies of the laminated windshield.

Figure 1:
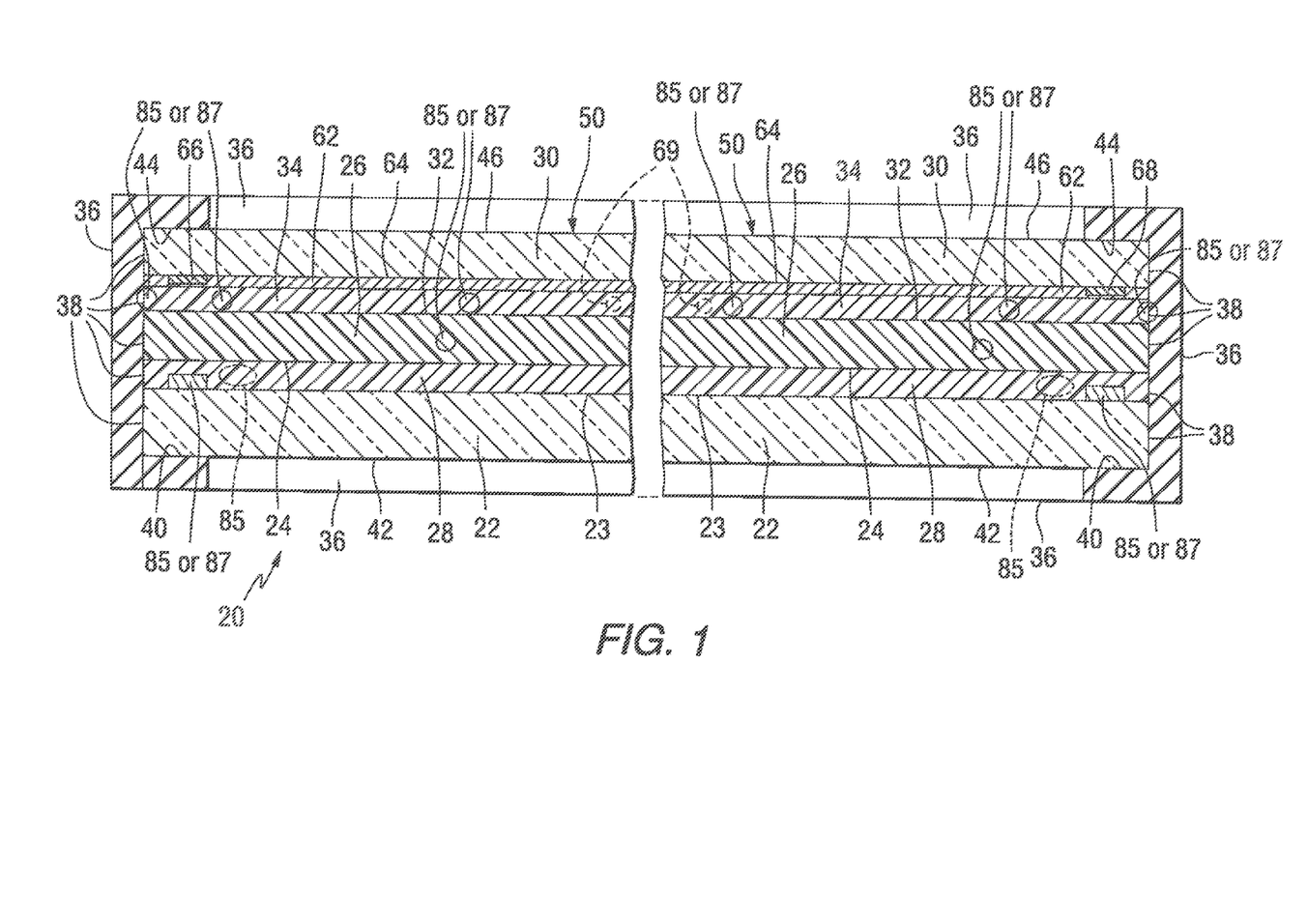
FIG. 1 is a cross sectional view of a non-limiting embodiment of an aircraft windshield incorporating features of the invention.

Shown in FIG. 1 is a non-limiting embodiment of an aircraft windshield 20 that can be used in the practice of the invention. The windshield 20 has a first glass sheet 22 secured to surface 24 of a vinyl-interlayer or sheet 26 by a first urethane interlayer 28, and has a second glass sheet 30 secured to surface 32 of the vinyl-interlayer 26 by a second urethane interlayer 34. An edge member or moisture barrier 36 of the type used in the art, e.g. but not limited to a silicone rubber or other flexible durable moisture resistant material is secured to (1) peripheral edge 38 of the windshield 20, i.e. the peripheral edge 38 of the first and second sheets 22 and 30, respectively; of the vinyl-interlayer 26; of the first and second urethane interlayers 28 and 34, respectively, (2) margins or marginal edges 40 of outer surface 42 of the windshield 20, i.e. the margins 40 of the outer surface 42 of the first glass sheet 22 of the windshield 20, and (3) margins or marginal edges 44 of outer surface 46 of the windshield 20, i.e. margins of the outer surface 46 of the second glass sheet 30.

As is appreciated by those skilled in the art and not limiting to the invention, the first glass sheet 22; the vinyl-interlayer 26 and the first urethane interlayer 28 form the structural part, or inner segment, of the windshield 20. The outer surface 42 of the windshield 20, which is the outer surface 42 of the glass sheet 22 faces the interior of the vehicle, e.g. but not limited to an aircraft (an aircraft that can be used in the practice of the invention, but not limiting to the invention, is shown in U.S. Pat. No. 8,155,816B2). The second urethane layer 34 and the second glass sheet 30 form the non-structural part, or outer segment, of the windshield 20. The outer surface 46 of the windshield 20 which is the surface 46 of the second glass sheet 30 faces the exterior of the aircraft. The second glass sheet 30 is part of a heatable member 50 that provides heat to remove fog from, and/or to melt ice on, the outer surface 46 of the windshield 20 in a manner discussed below.

As can be appreciated the invention is not limited to the construction of the windshield 20 and any of the constructions of aircraft transparencies disclosed in the art can be used in the practice of the invention. For example and not limited to the invention, the windshield 20 can include a construction wherein the vinyl interlayer 26 and the first urethane interlayer 28 are omitted, and the glass sheets 22 and/or 30 are plastic sheets.

Generally the glass sheets 22 and 30 of the windshield 20 are clear chemically strengthened glass sheets; however, the invention is not limited thereto, and the glass sheets 22 and/or 30 can be heat strengthened or heat tempered glass sheets. Further as is appreciated, the invention is not limited to the number of glass sheets, vinyl interlayers or urethane interlayers that make up the windshield 20, and the windshield 20 can have any number of sheets and/or interlayers.

Figure 2:
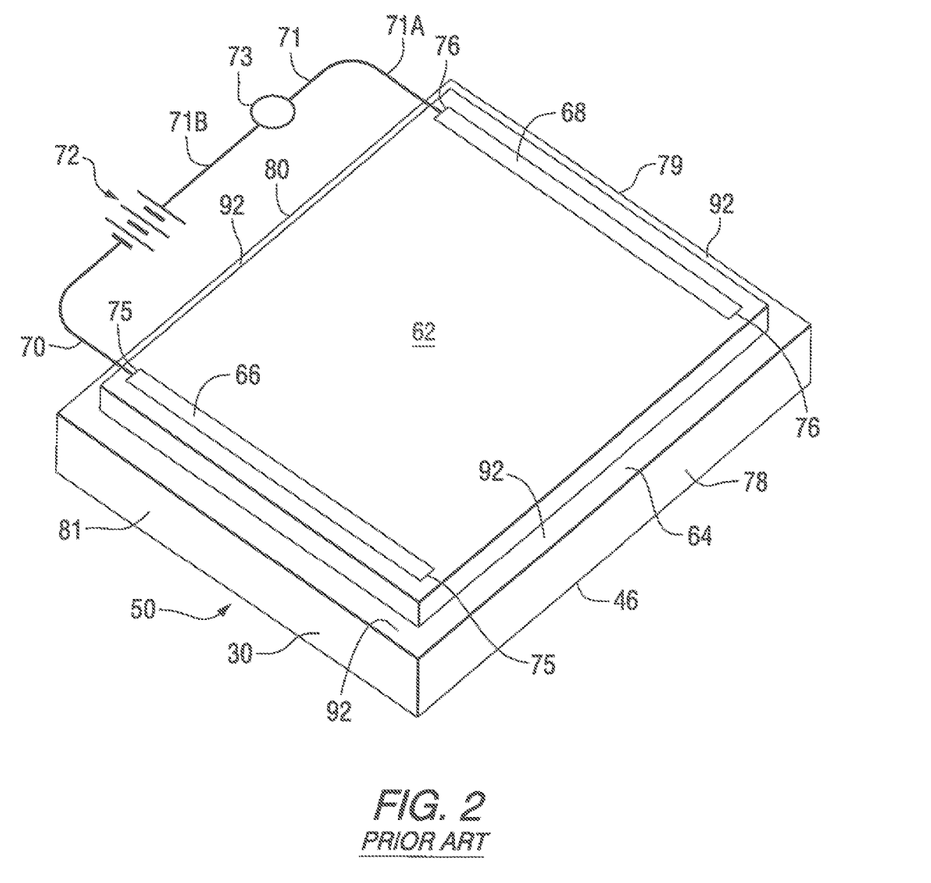
FIG. 2 is an isometric view of a prior art heatable member for removing fog, and melting ice and snow on the outer surface of the windshield.

The invention is not limited to the design and/or construction of the heatable member 50, and any electrically conductive heatable member used in the art to heat a surface of a glass or plastic sheet to melt ice on, and/or remove fog from the surface of the sheet can be used in the practice of the invention. With reference to FIG. 2, in one non-limiting embodiment of the invention, the heatable member 50 includes a conductive coating 62 applied to surface 64 of the second glass sheet 30, and a pair of spaced bus bars 66 and 68 in electrical contact with the conductive coating 62. The invention is not limited to the composition of the conductive coating 62, for example and not limiting to the invention; the conductive coating 62 can be made from any suitable electrically conductive material. Non-limiting aspects of conductive coatings that can be used in the practice of the invention include, but are not limited to a pyrolytic deposited fluorine doped tin oxide film of the type sold by PPG Industries, Inc. under the trademark NESA®; a magnetron sputter deposited tin doped indium oxide film of the type sold by PPG Industries, Inc. under the trademark NESA-TRON®; a coating made up of one or more magnetron sputter deposited films, the films including, but not limited to a metal film, e.g. silver between metal oxide films, e.g. zinc oxide and/or zinc stannate, each of which may be applied sequentially by magnetron sputtering, e.g. as disclosed in U.S. Pat. Nos. 4,610,771; 4,806,220 and 5,821,001, the disclosures of which in their entirety are hereby incorporated by reference.

As can be appreciated, the invention is not limited to the use of an electrically conductive coating to heat the glass sheet 60 and contemplates the use of any type of member that can be electrically heated, e.g. but not limited to electrical conducting wires. The wires, e.g. the wires 69 shown in phantom in FIG. 1 can be embedded in the second urethane interlayer 34 and electrically connected to the bus bars 66 and 68. Such a heating arrangement is known in the art under the PPG Industries Ohio Inc. registered trademark AIRCON and is disclosed in U.S. Pat. No. 4,078,107, which patent in its entirety is incorporated herein by reference.

The invention is not limited to the design and/or construction of the bus bars and any of the types of bus bars known in the art can be used in the practice of the invention. Examples of bus bars that can be used in the practice of the invention, include, but are not limited to, the types disclosed in U.S. Pat. Nos. 4,623,389; 4,820,902; 4,894,513; 4,994,650, and 4,902875, which patents in their entirety are hereby incorporated by reference. Each of the bus bars 66 and 68 are connected by a wire 70 and 71, respectively to a power source 72, e.g. a battery to flow current through the bus bars 66 and 68, and the conductive coating 62 to heat the conductive coating 62 and the second glass sheet 30 to remove ice and/or fog from the outer surface 46 of the windshield 20. A window heat controller 73 to provide electrical current to heat the coating 62 and to disconnect electrical current from the coating 62 is connected to one of the wires, e.g. the wire 71 such that wire section 71A of the wire 71 connects one pole of the window heat controller 73 to the bus bar 68, and the wire section 71B of the wire 71 connects another pole of the window heat controller 73 to the battery 72. With this arrangement, the window heat controller 73 can control the electrical power to the bus bars 66 and 68, and the conductive coating 62 to vary and/or regulate the current flow through the bus bars 68 and 66, and the conductive coating 62 to control the temperature of the conductive coating 62. Although not limiting to the invention, ends 75 of the bus bar 66, and ends 76 of the bus bar 68 are spaced from adjacent sides 78-81 of the glass sheet 30 to prevent arcing of the bus bars 66 and 68 with the metal body cover of the aircraft (shown in U.S. Pat. No. 8,155,816B2).

Figure 3:
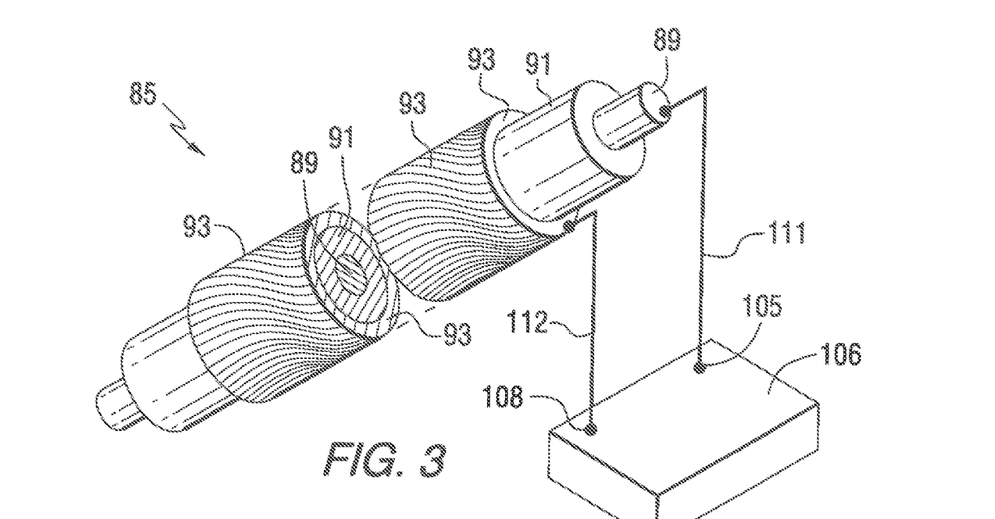
FIG. 3 is an isometric segmented view of a non-limiting aspect of a moisture sensor or detector of the invention.
Figure 4:
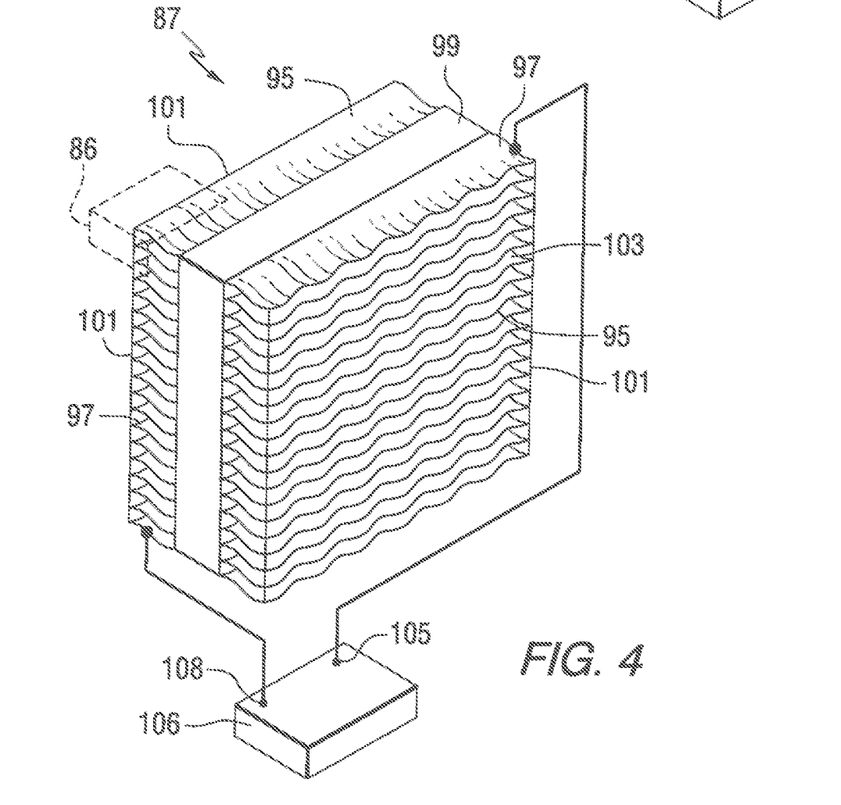
FIG. 4 is an isometric view of another non-limiting aspect of a moisture sensor or detector of the invention.

Shown in FIG. 3 is a moisture sensor 85, and shown in FIG. 4 is a moisture sensor 87; the moisture sensors 85 and 87 having features of the invention. More particularly, the moisture sensor 85 has a coaxial arrangement and includes, but is not limited to, a central electrical conductor or electrode 89, a dielectric sleeve 91 over the central electrical electrode 89, and an outer moisture pervious electrical conductive sleeve or outer electrode 93. The moisture sensor 87 shown in FIG. 4 includes a first outer moisture porous electrical conductive electrode 95 spaced from a second outer moisture porous electrical conductive electrode 97, and a dielectric layer 99 between and in physical contact, or close proximity, with the first and second electrodes 95 and 97, respectively. The dielectric can consist of any insulating material compatible with wire manufacturing, with preferably a large saturated moisture capacity, and with a melting temperature greater than the laminate processing temperature. Materials that can be used for the dielectric 91 or 99 include, but are not limited to, nylon of any chain length, e.g., nylon 4-6, nylon 6, nylon 6-6, nylon 6-12, nylon 11, polyamide-imide, polybenzimidazole, polyethersulfone or polysulfone. The moisture sensor 85 or 87 shown in FIG. 3 or FIG. 4, respectively can also include any number of additional moisture permeable conducting or insulating layers that do not substantially change the electrical response of the moisture sensor but may be desirable for fabrication or installation of the sensor, as is appreciated by those skilled in the art. A segment of a moisture permeable conducting or insulating layer 86 is shown in phantom in FIG. 4. The moisture sensors 85 and 87 are made of materials that are non-reactive with the materials of the windshield, e.g. but not limited to the glass sheets 22 and 30, the conductive coating 62, the vinyl interlayer 26 and the urethane interlayers 28 and 34. The electrodes 89 and 93 of the moisture sensor 85, and the electrodes 95 and 97 of the moisture sensor 87 are made of electrically conductive materials have a constant electrical conductivity over time at a fixed temperature. Materials that can be used for the electrodes 89 and 93 of the moisture sensor 85, and the electrodes 95 and 97 of the moisture sensor 87 include, but are not limited to the noble metals most commonly considered to be ruthenium, rhodium, palladium, silver, osmium, iridium, platinum, and gold, and non-noble metals and alloys such as, but not limited to, copper, tin-plated copper, nickel-plated copper, nickel-chromium, aluminum, and combinations thereof.

The central electrode 89 and the outer electrode 91 of the moisture sensor 85 preferably are made of the same material, and the outer electrodes 95 and 97 of the moisture sensor 87 are also preferably made of the same material to avoid chemical reaction between two different metals. In one aspect of the invention, the central electrode 89 of the moisture sensor 85 shown in FIG. 3 was made of a solid or stranded tin plated copper wire, and the outer electrode 93 of the moisture sensor 85 (see FIG. 3) and the outer electrodes 95 and 97 of the moisture sensor 87 (see FIG. 4) were made of a tin plated copper mesh to provide passageways 103 for moisture to move through the outer electrodes 93, 95 and 97 to contact the dielectric material 91 between the electrodes 89 and 93 of the sensor 85, and to move through the outer electrodes 95 and 97 of the sensor 87 to contact the dielectric layer 105 between the electrodes 95 and 97 of the moisture sensor 87. The invention is not limited to the thickness, size and number of passageways in the braid of the outer electrodes 93, 95 and 97. In the practice of the invention the outer mesh electrode was made of 44 AWG tin-plated copper wires with a 75% braid coverage.

The dielectric material 91 of the sensor 85 and the dielectric material 99 of the sensor 87 used in the practice of the invention is of the type that has increasing electric impedance as the moisture absorbed by the dielectric material increases. For purposes of clarity, impedance is the measurement of the opposition to current flow in a circuit. For direct current (DC) the only opposition is the resistance of the circuit. For alternating current (AC) the current is opposed by the inductance and capacitance as well as the resistance. The combination of inductance and capacitance is referred to as reactance and makes up the complex component of impedance, while resistance forms the real component. Quantitatively, impedance is defined as the complex ratio of the voltage to the current at a given frequency. For a sinusoidal input, the polar form of the complex impedance relates the amplitude and phase of the voltage and current. The magnitude of the polar impedance is the voltage to current amplitude ratio. The phase of the polar impedance is the phase shift between the current and voltage.

The impedance of the sensor 85 or 87 is measured by the electrical measurement mechanism 115 (see FIG. 5) at one or more frequencies. As appreciated by those skilled in the art the impedance in general and the reactive impedance in particular of the sensor 85 or 87 can be related to the moisture content of the sensor 85 or 87 through the use of a suitable model and or calibration curve, illustrated in a non-limiting embodiment by FIG. 9. Moisture permeation into the dielectric 91 in FIG. 3 or 99 in FIG. 4 primarily causes an increase in the capacitive component of the reactive impedance of the sensor. Similarly, through the use of a calibration routine the moisture content of the sensor 85 or 87 can be related to the moisture content of the materials in immediate contact with the sensor, such as the vinyl interlayer 26 or the urethane interlayers 28 and/or 34.

The thickness of the moisture sensors 85 and 87 is not limiting to the invention, however, in the practice of the invention, when the moisture sensor 85 or 87 is positioned between sheets, the thickness of the moisture sensor 85 or 87 is preferably limited to a thickness such that the moisture sensor can be positioned within a layer spaced from the layer on each side of the moisture sensor. More particularly, with reference to FIG. 1, the moisture sensors 85 or 87 shown in FIG. 1 are positioned in the plastic laminate layer 26, 28 and/or 34; the first urethane layer 28 having a thickness of 0.060 inch as measured between the surface 23 of the first glass sheet 22 and the surface 24 of the vinyl interlayer 26. The moisture sensor 85 preferably has a diameter of less than 0.060 inch, or the moisture sensor 87 has a thickness measured between outer surface 101 of the electrodes 95 and 97 of the moisture sensor 87 to secure the moisture sensor 85 or 87 in the first urethane layer 28. As can be appreciated, when the moisture sensors 85 and 87 are placed on the periphery 38 of the windshield 20 within the moisture seal 36 (see FIG. 1), the thickness of the moisture sensors 85 and 87 is less than the thickness of the windshield as measured between the inner surface 42 and the outer surface 46, of the windshield 20 (see FIG. 1).

A moisture sensor 85 was made. The center electrode 89 was made of 28 AWG 7/36 tin plated stranded copper wire. The dielectric sleeve 91 was made of nylon 6 purchased from Honeywell and sold under the trademark Aegis H55WC Nylon Jacket Compound. The nylon was extruded over the center electrode 89 to a nominal wall thickness of 0.005 inch. The outer electrode 93 was made of 44 AWG tin plated copper braid, braided over the dielectric sleeve 91 with a nominal 75% coverage. An outer insulating layer (numbered 86 and shown only in FIG. 4 and only in phantom) consisting of Aegis H55WC Nylon Jacket Compound was extruded over the braid to a nominal outside diameter of 0.045 inch. A moisture sensor 87 was also made. The dielectric material 99 of the moisture sensor 87 had a range of thicknesses from 0.001 inch to 0.032 inch with a non-limiting width of 0.5 inch. The length varied depending on the size of the windshield and the area to be monitored by the moisture sensor. The dielectric layer 99 of the sensor 87 consisted of the same dielectric material used for the dielectric sleeve 91 of the moisture sensor 85 (see FIG. 3). The electrodes 95 and 97 of the moisture sensor 87 were made of nickel plated copper metalized polyester fabric tape, with conductive pressure sensitive acrylic adhesive, nominally 0.25 inch wide. The electrodes 95 and 97 of the moisture sensor 87 were joined to one pair of opposite surfaces of the dielectric material 99 by conductive pressure sensitive acrylic adhesive.

As is appreciated by those skilled in the art a dielectric material or dielectric for short is an electrical insulator that can be polarized by an applied electric field. When a dielectric is placed in an electric field, electric charges do not flow through the material as they do in a conductor, but only slightly shift from their average equilibrium positions causing dielectric polarization. Because of dielectric polarization, positive charges are displaced toward the field and negative charges shift in the opposite direction. This creates an internal electric field that reduces the overall field within the dielectric itself. If a dielectric is composed of weakly bonded molecules, those molecules not only become polarized, but also reorient so that their symmetry axes align to the field. The moisture sensor having a coaxial structure can function as an impedance moisture sensor or as a reactive moisture sensor. The electrical impedance, i.e. the capacitance, resistance and complex impedance of the moisture sensor changes. Once the moisture starts to ingress into the cockpit layer system, a sensor that consists of the electrical power supply and sensors for the capacitance, resistance and/or complex impedance will detect these changes.

In the coaxial structure (FIG. 3) or the stripline structure (FIG. 4) the "outside insulation" represents the material matrix in which the sensor is embedded. For instance the outside insulation can consist of inter layer resin or material that surround the laminate. The wire mesh comprising the outer electrode of the coaxial pair was selected for moisture permeability, electrical conductivity and chemical compatibility. The central conductor in the preferred practice of the invention is selected primarily for electrical conductivity and chemical compatibility. The responsive dielectric can change resistivity and/or dielectric constant upon absorption of moisture. The moisture to be sensed moves from the outside insulation through the outer conductor and into the responsive dielectric. The coaxial geometry of the moisture sensor 85 (see FIG. 3) has the additional advantage of superior immunity to electrical interference, relative to the stripline geometry of the moisture sensor 87 (see FIG. 4) since the wire mesh can be held at aircraft ground or floating ground potential to provide electrical shielding of the inner conductor 89 of the moisture sensor 85.

The purpose of the moisture measurement is not simply to measure the instantaneous water ingression rate between sheets of the aircraft laminated windshield, but also the quantity of moisture accumulated over time. The history of the moisture ingression is just as important as the absolute concentration of the water in the window system. The concept of the window moisture measurement is based on the electrical property changes of a sensor element following moisture ingression between the sheets of the windshield. A sensor system includes, but is not limited to, the moisture sensor together with the electrical power supply, circuitry and software that detects the changes and communicates the changes to the persons responsible for maintaining the aircraft in a safe operating condition, e.g. as disclosed in U.S. Pat. No. 8,155,816B2, which patent is hereby incorporated by reference.

In one non-limiting embodiment of the invention, the moisture sensor 85 and/or 87 is based on the predictable increase in complex impedance (ohms) resulting from the dielectric sleeve 91 of the sensor 85 or the dielectric 99 of the sensor 87 absorbing moisture. More particularly, the center electrode 89 as shown in FIG. 3 is connected to one pole 105 of an AC power supply 106, and the outer electrode 93 is connected to a second pole 108 of the AC power supply 106 (see FIG. 5). As for the moisture sensor 87, the first outer electrode 95 is connected to the pole 105 of the AC power supply 106, and the second outer electrode 97 is connected to the pole 108 of the power supply 106. Voltage is applied to the electrodes and the impedance of the circuit measured. As the dielectric absorbs moisture the impedance increases.

Figure 5:
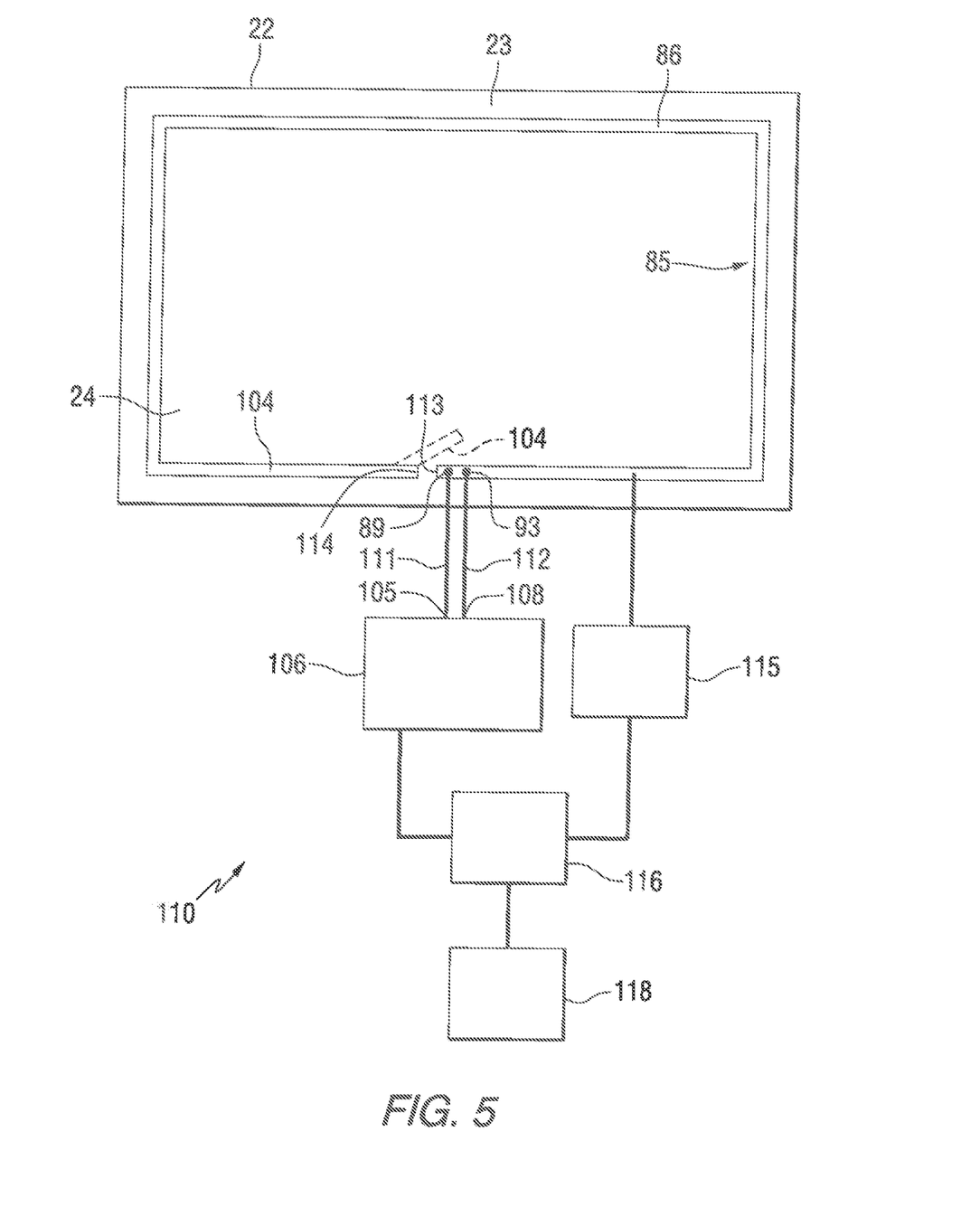
FIG. 5 is a non-limiting embodiment of an electrical system to monitor and act on the output signals of the moisture sensor in accordance to the teachings of the invention.

The invention is not limited to the circuit employed to measure the electrical changes when moisture is absorbed by the dielectric. Shown in FIG. 5 is a non-limiting embodiment of an electrical system 110 that can be used with the sensors 85 and 87 to determine moisture penetration in the windshield 20. In the following discussion, the invention will be discussed using the moisture sensor 85 shown in FIG. 3. Unless indicated otherwise, the discussion of the invention using the sensor 85 is applicable to the practice of the invention using the sensor 87. In the non-limiting aspect, of the invention shown in FIG. 5, the moisture sensor 85 is applied to the surface 23 of the glass sheet 22 and secured against the surface 23 of the first glass sheet 22 in any usual manner, e.g. but not limiting to the invention by the first urethane interlayer 28 (see FIG. 1). As can be appreciated, the coaxial moisture sensor 85 can be integrated in any plastic laminate member (28, 26 and 34). In the non-limiting embodiment of the invention shown in FIG. 5, the coaxial moisture sensor 86 is mounted over the surface 23 of the first glass sheet 22 of the windshield 20 and extends around substantially the entire marginal edges of the first glass sheet 22. The coaxial moisture sensor 85 has a first termination surface designated by the number 89 (the central electrode of the sensor 85) and a wire 111 connecting the central electrode 89 to the pole 105 of the AC power supply 106, and a second termination surface designated by 93 (the outer electrode 93 of the sensor 85) and a wire 112 connecting the outer electrode 93 to the pole 108 of the AC power supply 106 to apply a voltage to the moisture sensor 85. In FIG. 5 there is shown a separation between the ends 113 and 114 of the sensor 85. The separation between the ends 113 and 114 is not limiting to the invention, and the ends 113 and 114 of the sensor 85 can overlap one another as shown in phantom in FIG. 5.

The power source 106 of the electrical system 110 can be any conventional electrical source, such as, but not limited to, a battery, an electrical generator, and the like to apply a voltage to the moisture sensor 85. The electrical system 110 further includes an electrical measurement mechanism 115 to measure complex impedance (ohm) of the moisture sensor 85. A control mechanism 116, such as embedded electronics or software on a computer, is used to control and communicate with both the electrical power source 106 and the electrical measurement mechanism 115. The control mechanism 116 can be used to command the electrical power source 106 to provide a specifically set electrical potential to the moisture sensor 85 and, after application, the control mechanism 116 can collect and/or calculate the electrical potential of the moisture sensor 85 via the electrical measurement mechanism 115. All of the electrical power source 106, the electrical measurement mechanism 115, and the control mechanism 116 can be combined in a single unit or instrument, e.g. a console of the type shown in FIG. 18 of, and disclosed in, U.S. Pat. No. 8,155,816B2 or can be individual units as shown in FIG. 5. The electrical measurement system can be any commonly used system used for measuring impedance or capacitance, two such examples are described below for completeness.

In one non-limiting embodiment of the invention, an impedance measurement is made by way of analyzing the phase shift of a known frequency applied to the sensing element 85. As mentioned above, the electrical power source 106 is connected to one electrode 89 through the wire 111, and the power source 106 is connected to the other electrode 93 of the sensor 85 through the wire 112. This connection allows the moisture sensor 85 to act as an electrical circuit when the electrical power source 106 applies an electrical potential. The electrical power source 106 applies an AC voltage to the moisture sensor 85, as set or specified by the control mechanism 116. This applied voltage results in a measured potential on sensor 85 (measured by electrical measurement mechanism 115) that is different in phase and magnitude from the applied voltage. Since the electrical power source 106 is applying a set voltage, and the electrical measurement mechanism 115 is reading or measuring the voltage difference on moisture sensor 85, the electrical measurement mechanism 115 (or the control mechanism 116, or any connected system) is able to calculate the complex impedance (ohm) from the voltage magnitude and phase difference between the central electrode 89 and outer electrode 93 of the moisture sensor 85. The complex impedance is then used to indicate the amount of moisture absorbed by the dielectric material 91 of the moisture sensor 85 or the dielectric material 99 of the moisture sensor 87. The electrical signal frequency used for this measurement is typically chosen to maximize the response of the sensing element to moisture change however multiple frequencies can be used to improve accuracy and reduce the impact of noise.

In another non-limiting embodiment of the invention an impedance measurement is made by way of DC voltage is applied across the electrodes and the charge time is measured (time it takes for the sensing element to reach the applied DC voltage). The electrical power source 106 applies a DC voltage to the moisture sensor 85, again as set or specified by control mechanism 116. This applied voltage results in a measured potential difference (from electrical measurement mechanism 115) on sensor 85 that will approach the applied voltage. The electrical measurement mechanism 115 (or the control mechanism 116) is able to calculate the capacitance (farads) of the moisture sensor 85 based on the time to reach the applied voltage. The capacitance of the sensing element is then used to indicate the amount of moisture absorbed by the dielectric material 91 of the moisture sensor 85 or the dielectric material 99 of the moisture sensor 87. In order to obtain continuous measurements, a changing DC voltage can be used as well as measurement of both charge and/or discharge times.

The invention described can use the above described methods, or any other impedance measurement systems including series and/or parallel resistance measurement using a current and voltage relationship. Additionally the invention can use a combination of impedance measurement systems at the same time, sequentially, or selectively based on the measurement condition.

More particularly, when moisture penetrates the windshield 20, the moisture will eventually reach the dielectric material 91 of the moisture sensor 85 and/or the dielectric material 99 of the moisture sensor 87. As the moisture reaches the dielectric material 91 and/or 99 of the moisture sensor 85 and/or 87, respectively, the moisture begins to be absorbed by the dielectric material. As the dielectric material continues to absorb moisture the dielectric material becomes saturated with moisture and no longer significantly absorbs moisture. The absolute moisture content of the dielectric material depends on the thickness, and absorption coefficient, of the dielectric material. In the practice of a non-limited aspect of the invention, when the measured complex impedance of the moisture sensor 85 and/or 87 is at a predetermine value indicating that moisture absorption by the dielectric material 91 and/or 95 is at a predetermined value, the control mechanism 116 sends a signal to the alarm 118 to advise the crew of the aircraft and/or other personnel as disclosed in U.S. Pat. No. 8,155,816B2 of a moisture penetration issue. In another non-limiting embodiment of the invention, the moisture content of moisture sensor 85 and/or 87 is monitored (either continuously or intermittently) and the trending of moisture content over time is analyzed to advise the crew of the aircraft and/or other personnel of an issue with the windshield.

The arrangement of the moisture sensor 85 shown in FIG. 5 can be used to indicate that moisture has penetrated through or around the sealant 36 and entered the volume between the glass sheets 22 and 30 (see FIG. 1). However using a single strip, 104, of the moisture sensor 85 and 87, does not indicate where the moisture penetration occurred, how far the moisture has penetrated, or which side of the windshield the moisture has penetrated. In order to enhance identifying the moisture penetration areas between the glass sheet 22 and the vinyl interlayer 26, multiple strips 104 can be placed in a grid or array pattern over the inner surface 23 of the sheet 22.

Figure 6:
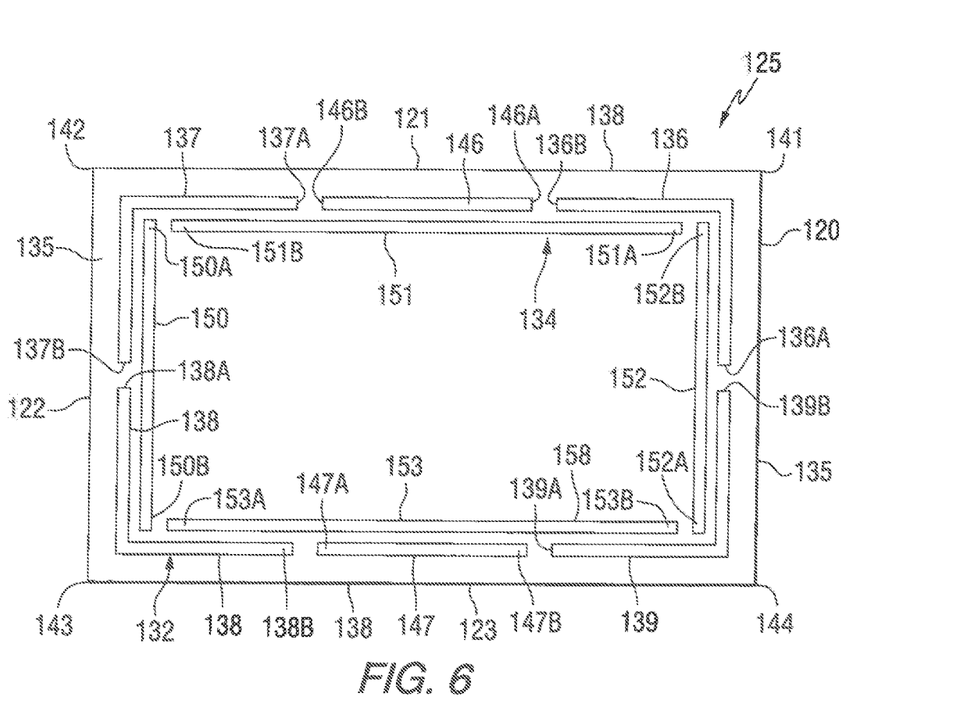
FIG. 6 is a plan view of a non-limiting embodiment of an arrangement of moisture sensors or detectors to estimate approximate position of moisture penetration and depth of moisture penetration.

In the non-limited embodiment of the invention shown in FIG. 6, each one of sides 120-123 of glass sheet 125 has two rows 132 and 134 of moisture sensors at or adjacent to the margin 135 of glass sheet 125 to provide an array of moisture sensors to more definitively identify where a moisture area in the windshield is present. Although the non-limited embodiment of the invention under discussion references the sheet 125 (FIG. 6), the discussion is applicable to the glass sheets 22 and 30, the vinyl interlayer 26 and urethane interlayers 28 and 34 unless indicated otherwise. Further, although reference in the following discussion is made to moisture sensors having different number designations, unless indicated otherwise the moisture sensors mentioned below include the moisture sensor 85 of FIG. 3 and moisture sensor 87 of FIG. 4.

With reference to FIG. 6, the first row 132 of moisture sensors 136-139 are at corners 141-144, respectively of the sheet 125, and moisture sensors 146 and 147 are at the sides 121 and 123, respectively of the sheet 125. End 136A of the moisture sensor 136 is adjacent to and spaced from end 139B of the moisture sensor 139 at the side 120 of the sheet 125; end 136B of the moisture sensor 136 is spaced from and adjacent to end 146A of the moisture sensor 146, and end 146B of the moisture sensor 146 is adjacent to and spaced from end 137A of the moisture sensor 137, at the side 121 of the sheet 125; end 137B of the moisture sensor 137 is adjacent to and spaced from the end 138A of the moisture sensor 138 at the side 122; end 138B of the moisture sensor 138 is adjacent to and spaced from end 147A of the moisture sensor 147, and end 147B of the moisture sensor 147 is adjacent to and spaced from end 139A of the moisture 139, at the side 123, of the sheet 125.

The second row 134 of the moisture sensors includes moisture sensors 150-153. The moisture sensor 150 extends between sides 121 and 123 of the glass sheet 125; has its end 150A adjacent to and spaced from end 151B of the moisture sensor 151, and its end 150B adjacent to and spaced from end 153A of the moisture sensor 153. The moisture sensor 151 extends between sides 122 and 120 of the glass sheet 125 and has its end 151A adjacent to and spaced from end 152B of the moisture sensor 152. The moisture sensor 152 extends between sides 121 and 123 of the glass sheet 125 and has its end 152A adjacent to and spaced from end 153B of the moisture sensor 153. The moisture sensor 153 extends between sides 120 and 122 of the glass sheet 125 and has its end 153B adjacent to and spaced from end 152A of the moisture sensor 152.

The ends A and B of each of the moisture sensors 136-139, 146, 147 and 150-153 are individually electrically connected to the electrical power source 106 as shown in FIG. 4 to apply an electrical potential to the moisture sensors 136-139, 146, 147 and 150-153, and to the electrical measurement mechanism 115 for measuring the electrical potential of the moisture sensors 136-139, 146, 147 and 150-153. In another aspect of the invention, the end A or B of each of the moisture sensors 136-139, 146, 147 and 150-153 are individually electrically connected to the electrical power source 106 as shown in FIG. 3 to apply an electrical potential to the moisture sensors 136-139, 140, 147 and 150-153, and to the electrical measurement mechanism 115 for measuring the complex impedance of the moisture sensors 136-139, 146, 147 and 150-153. The control mechanism 116 controls and communicates with both the electrical power source 106 and the electrical measurement mechanism 115 as discussed above to command the electrical power source 106 to provide a predetermined or specifically set electrical potential to the electrodes 89 and 93 of the moisture sensor 85 and/or electrodes 95 and 97 of the moisture sensor 87 and to electrodes of the moisture sensors 136-139, 148, 147 and 150-153 and, after application, the control mechanism 116 can collect and/or calculate the electrical potential of the moisture sensors 85, 87 and 136-139, 146, 147 and 150-153 via the electrical measurement mechanism 115. All of the electrical power sources 106, the electrical measurement mechanisms 115 and the control mechanisms 116 for the moisture sensors 85, 87 and 136-139, 146, 147 and 150-153 can be combined in a single unit or instrument, e.g. a console of the type disclosed in U.S. Pat. No. 8,155,816B2, or can be individual units.

With continued reference to FIG. 6, the arrangement of the two rows 132 and 134 each having spaced moisture sensors, e.g. moisture sensors 136-139, 146 and 147 in the row 132, and the moisture sensors 150-153 in the row 134 provides for a closer approximation to area of moisture penetration. More particularly and not limiting to the invention, moisture is absorbed by the dielectric material 91 and/or 99, positioning moisture penetration 156 in the center area of the side 121 of the sheet 125; moisture is absorbed by the moisture sensors 139 and 153, positioning the moisture penetration 158 in the side 123 adjacent the side 138 of the sheet 125.

The moisture sensor 85 and/or 87 can be applied to a surface of one or more of the glass sheets 22 and 30. As is appreciated, when moisture sensors of the invention are placed on more than one sheet, each one of the moisture sensors preferably has its own electrical power source 106, or one power source is provided and is electrically connected to two or more of the moisture sensors. Similarly, one or multiple electrical measurement mechanisms 115 can be used to read and measure the electrical potential or current flowing through each of the moisture sensors on the glass sheets 22 and 30, and the vinyl interlayer 28, of the windshield 20. In this manner the output of each one of the moisture sensors on the sheets 22, 28 and 30 can be monitored.

Figure 7:
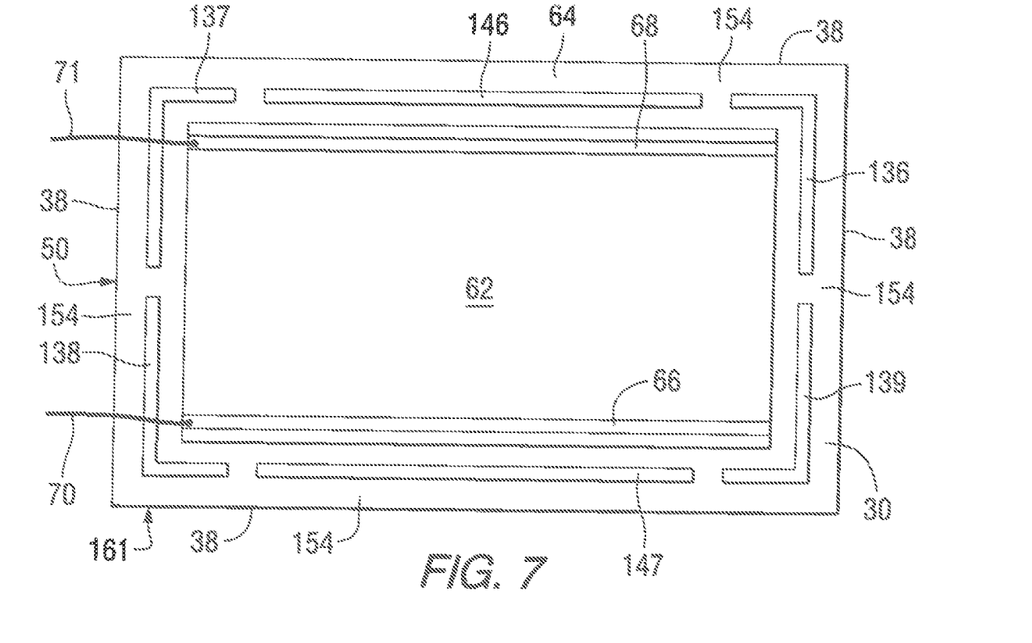
FIG. 7 is a plan view showing the moisture sensor of the invention surrounding the heatable member shown in FIG. 2.

With reference to FIG. 7, there is shown the heatable member 50 having the conductive coating 62 applied to the inner surface 64 of the second glass sheet 30. As can be appreciated by those skilled in the art, the moisture sensors 136-139, 146 and 147 are spaced from the bus bars 66 and 68, and from the conductive coating 62, to electrically isolate the moisture sensors from the bus bars 66 and 68, and from the conductive coating 62, of the heatable member 50. In one non-limiting aspect of the invention, e.g. as shown in FIG. 7, the bus bars are within the perimeter of the coating 62, and the perimeter of the conductive coating 62 is spaced from sides 38 of the glass sheet 30. The moisture sensors 136-139, 146 and 147 are applied on uncoated portion 154 of the surface 64 of the glass sheet 30 between the sides 38 of the sheet 30 and the conductive coating 62. The uncoated portion 154 of the glass surface 62 can be provided in any convenient manner, e.g. by masking the glass surface during the coating process, or abrasively or chemically removing the coating from the glass surface. Because the glass is chemically strengthened it is preferred to mask the areas during the coating process to avoid surface damage that can cause the tempered glass to fracture.

Figure 8:
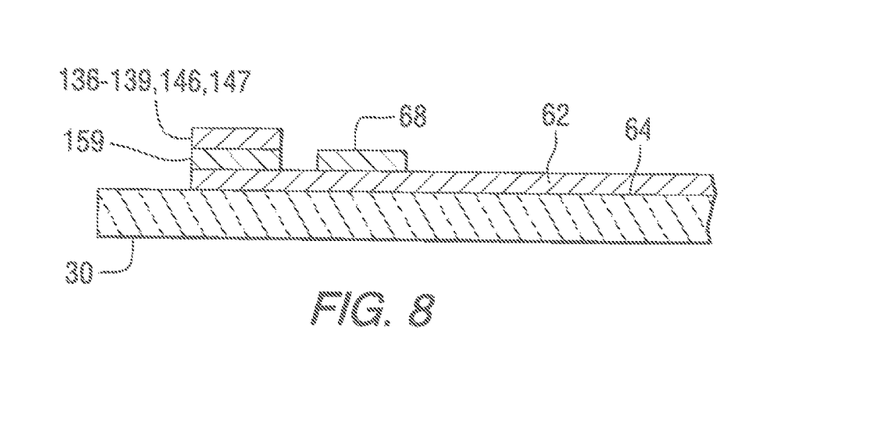
FIG. 8 is an elevated cross sectional side view showing a non-limiting embodiment of the invention for mounting a sensor over a bus bar of a heatable member.

As can be appreciated, the invention contemplates positioning moisture sensors of the invention over the conductive coating 62 and/or the bus bars 66 and 68. More particularly, as shown in FIG. 8, the moisture sensors 136, 139, 145 and 147 are applied over the electrically conductive coating 62. To electrically isolate the outer electrode 93 of the moisture sensor 85 shown in FIG. 3, and/or one or both the electrodes 95 and 97 of the moisture sensor 87 shown in FIG. 8 a moisture permeable, electrically nonconductive outer insulator 159 extends under the moisture sensors 136-139, 146 and 147 electrically isolate the coating 62 and moisture sensors 136-139, 146 and 147. Materials that can be used in the practice of the invention, but not limited thereto include nylon (of any chain length previously listed), urethane, polyvinyl butyral or polyimide. The layer 159 can have an adhesive layer on each surface to secure one or more of the moisture sensors in position during the handling of the sheets prior to the lamination of the sheets, or can be held in place using any practical means consistent with the practices of laminated windshield manufacture. As can be appreciated, the moisture sensor can decrease visibility through that portion of the glass sheet over which it is deposited, and therefore, for the moisture sensors that extend into the vision area of the windshield, the maximum width of the moisture sensor depends upon the required or specified operator viewing area through the windshield 20. Aircraft transparencies, e.g. windshields have specific safety requirements specifying, among other things, the size of the viewing area of the windshield.

Figure 9:
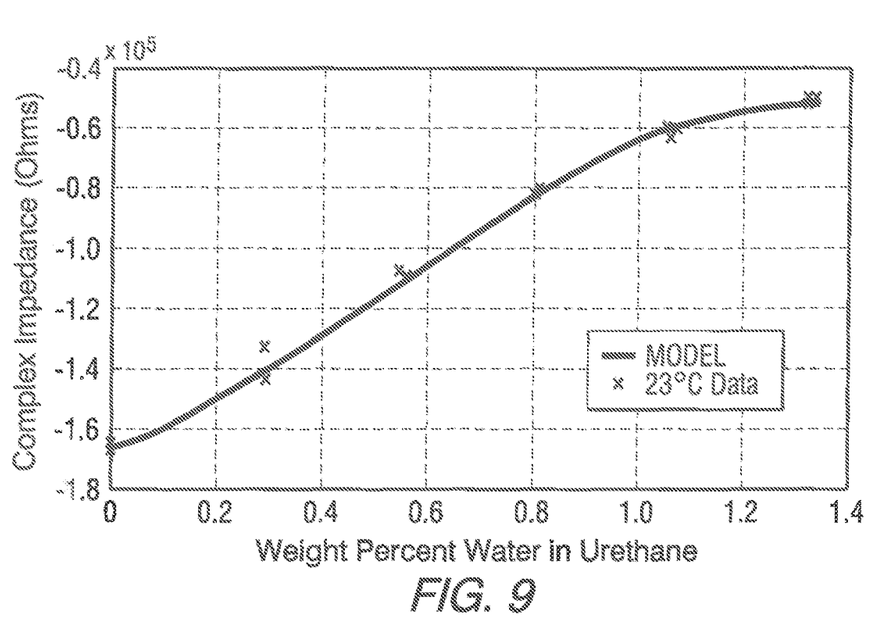
FIG. 9 is a graph showing changes in complex impedance (ohms) as a function of moisture content in wt. % for a dielectric material.

The complex impedance (ohm) output of the moisture sensor of the invention can be measured using a variety of standard readout sensor circuits, e.g. of the type disclosed in US Published Patent application 2015/0137837A1 and of the type shown in FIG. 5. Shown in FIG. 9 is a graph showing the performance of the moisture sensor shown in FIG. 3. With reference to FIG. 9, the "y" or vertical axis is the imaginary component of the complex impedance (ohms) and the "x" or horizontal axis is the moisture content of the urethane layer 28 or 34 in percent. The graph shown in FIG. 9 is a model (solid curve) with one set of recorded data for the complex impedance (ohms) of the sensor 85 shown in FIG. 3. The weight of all sensors with their associated connection wires were recorded prior to lamination. The laminate or coupons were fabricated with urethane of the type sold by PPG Industries, Inc. under the trademark PPG112, incorporating a moisture sensor of the type 85 show in FIG. 3, and with the glass plies removed after lamination. The composition of the PPG112 interlayer is disclosed in U.S. Pat. No. 4,704,174, which patent in its entirety is hereby incorporated by reference. After removal of the glass plies the coupons were initially dried in a vacuum oven set at nominally 50° C. until the weight change between measurements 24 hours apart was less than 5 milligrams, and the "dry" starting weight recorded. The coupons were then enclosed in individual glass desiccator jars, with vacuum grease seals between all mating parts, containing a predetermined quantity of water and left to equilibrate for 1 month. The coupons were removed, immediately weighed and the complex impedance (ohms) measured. The conversion from impedance to moisture is possible through use of standard transmission line or capacitor equations by replacing the dielectric constant of the inner dielectric with a moisture dependent equation. Equations for conversation from impedance to moisture are known in the art and further discussions not deemed necessary.

The discussion is now directed to non-limited embodiments of the invention relating to the placement of the non-limiting embodiments of moisture sensors or detectors of the invention on selected components of the windshield 20, to detect the presence of moisture and/or measure the amount of moisture present between the sheets, e.g. but not limited to, between the glass sheets 22 and 30, in accordance to the teachings of the invention.

Figure 10:
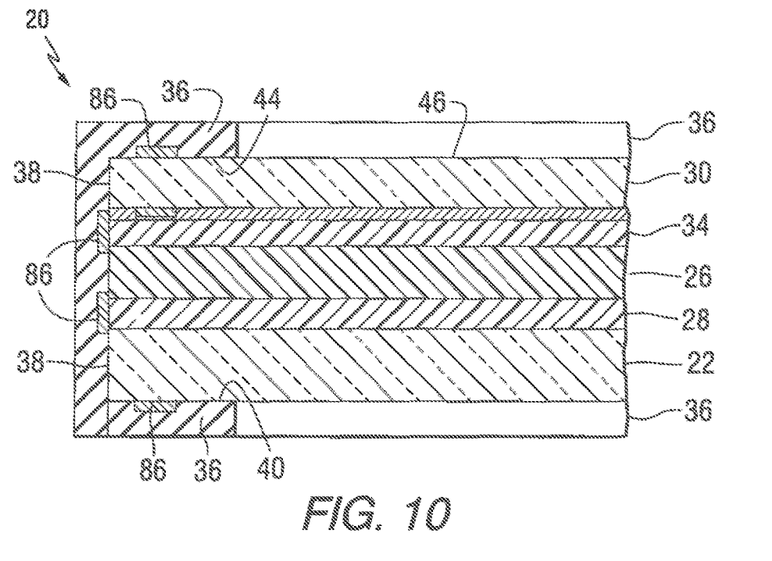
FIG. 10 is a cross section view of a segment of the windshield shown in FIG. 1 showing the position of moisture sensors or detectors at the marginal and peripheral edge portions of the aircraft windshield in accordance to the teachings of the invention.

As critical as the measurement principle and type, where the moisture sensor should be located will determine if the new sensor can effectively detect the moisture ingress and provide early enough warning for the "Intelligent Window" sensor system to alarm the pilot. With reference to FIG. 1 as needed, the placement of the moisture sensor 85 (FIG. 3), or 87 (FIG. 4) or multiple strips (FIGS. 6 and 7) can be applied to any position on or between the glass sheets 22 and 30 as shown in FIGS. 1 and 10. Further, the invention is not limited to the number of moisture sensors and/or the location of the moisture sensor on the windshield. More particularly and not limiting to the invention, the moisture sensor can be embedded in the first urethane layer 28 between the glass sheet 22 and the vinyl interlayer 26, embedded in the vinyl interlayer 26; embedded in the second urethane layer 28 between the glass sheet 30 and vinyl interlayer 26.

In the non-limited embodiments of the invention discussed above, the moisture sensor 85 and 87, in general, has the function of measuring the presence and time period that moisture is in contact with the moisture sensor of the invention. The invention, however, is not limited thereto, and the moisture sensor of the invention can be used to measure the presence and time period that moisture is in contact with the moisture sensor and to activate and deactivate electrical equipment, e.g. as discussed below and in U.S. Pat. No. 8,155,816B2.

Control System

Disclosed in U.S. Pat. No. 8,155,816B2, which patent is hereby incorporated by reference, is a method and apparatus to monitor the performance of a transparency, e.g. but not limited to the windshield 20 of the invention and to timely schedule maintenance of, e.g. repairs to, or replacement of, transparencies, e.g. aircraft windshields that are performing outside acceptable limits. In this particular instance, performing outside of acceptable limits as a result of moisture penetration.

In general the output of the sensors carrying data regarding the performance of moisture barrier of the windshield are connected to a console including a computer having software to read and analyze the signals from the moisture sensors or detectors to monitor and/or determine the performance of the windshield. A monitor can be used in the practice of the invention to provide visual display, and a speaker to provide an audio, regarding the performance of the windshield. The console can include an alarm to bring attention to the monitor. Placing the console in the aircraft provides the personnel within the aircraft with real time performance of the windshield.

In another embodiment disclosed in U.S. Pat. No. 8,155,816, the console has a wireless transmitter and receiver; the transmitter transmits signals to a transmitting tower. The signals carry data on the performance of the windshield 20 are transmitted to a control center (not shown). The data received is studied and the appropriate action to be taken is scheduled, e.g., based on the information received, personnel at the control center determine what action, if any, is needed. If action such as repairs to the windshield or replacement of the windshield, is needed, a signal providing a repair schedule is transmitted to the satellite to a maintenance center geographically close to the designated repair location (usually the next scheduled stop for the aircraft) to arrange to have all parts, equipment and personal need at the designated repair location.

The invention is not limited to the embodiments of the invention presented and discussed above which are presented for illustration purposes only, and the scope of the invention is only limited by the scope of the following claims and any additional claims that are added to applications having direct or indirect linage to this application.

What is claimed is:

1. An aircraft windshield comprising:
a plurality of sheets joined together to provide a laminated window having a vision area, the window having a moisture seal on peripheral and marginal edge portions of the sheets;
a moisture sensor positioned between the sheets and/or between the sheets and the moisture seal, wherein the moisture sensor comprises a dielectric material comprising at least one of an extruded sleeve and an extruded layer formed from an absorbent extruded polymer material, between a first electrode and a second electrode, wherein the dielectric material is in electrical contact with the first and second electrodes and maintains the first and the second electrodes spaced from one another and out of surface contact with one another; and
sensor electronics operatively connected to the electrodes of the moisture sensor to measure an electrical property of the moisture sensor to determine an amount of moisture absorbed by the dielectric material, wherein the sensor electronics comprise:
a power source for applying alternating electrical current to the first and the second electrodes; and
an electrical measurement mechanism configured to measure a complex impedance (ohms) of the dielectric material and to indicate an amount of moisture within the laminated window in an area of the moisture sensor based on the measured complex impedance.

2. The aircraft windshield according to claim 1, wherein the electrical measurement mechanism is configured to measure capacitance and resistance changes of the dielectric material due to moisture absorbed by the dielectric material.

3. The aircraft windshield according to claim 2, wherein the absorbent extruded polymer comprises nylon 4-6, nylon 6, nylon 6-6, nylon 6-12, nylon 11, polyamide-imide, polybenzimidazole, polyethersulfone, polysulfone, and/or combinations thereof.

4. The aircraft windshield according to claim 1, wherein:
the moisture sensor has a coaxial shape and the dielectric material has an elongated shape with a center hole,
the first electrode comprises an outside sleeve having a plurality of spaced holes through a wall of the first electrode,
the first electrode is in surface contact with an outer surface of the dielectric material,
the second electrode comprises a wire, and
the dielectric material is extruded over the wire, such that the first electrode is in surface contact with an inner surface of the dielectric material.

5. The aircraft windshield according to claim 1, wherein the first and the second electrodes are made of a material selected from: ruthenium, rhodium, palladium, silver, osmium, iridium, platinum, gold; alloys of tin plated copper, nickel-chromium, aluminum; and/or combinations thereof.

6. The aircraft windshield according to claim 4, wherein a thickness of the dielectric material extruded over the wire is between 0.001 inch and 0.032 inch.

7. The aircraft windshield according to claim 1, wherein the dielectric material has an elongated shape having a first surface and a second surface, the first electrode is in electrical contact with the first surface of the dielectric material and the second electrode is in electrical contact with the second surface of the dielectric material, and the first and the second electrodes are only electrically connected to one another by way of the dielectric material and the first and the second electrodes each have a plurality of spaced holes extending through walls of the respective electrodes.

8. The aircraft windshield according to claim 7, wherein the dielectric material has a 4-sided cross section with the first electrode mounted on a side of the dielectric material designated as the first side of the dielectric material and the second electrode is mounted on a side of the dielectric material opposite to the first side.

9. The aircraft windshield according to claim 7, wherein a thickness of the dielectric material between the first surface and the second surface thereof is between 0.001 inch and 0.032 inch.

10. The aircraft windshield according to claim 1, wherein the moisture seal overlays the marginal edge portions and the peripheral edge portions of the laminated window.

11. The aircraft windshield according to claim 1, wherein:
the plurality of sheets comprises two or more transparent sheets joined together by an adhesive, and
the moisture sensor is positioned on a surface portion of at least one of the sheets.

12. The aircraft windshield according to claim 1, wherein each of the sheets comprises a first major surface opposite to a second major surface, and a peripheral surface joining the first major surface and the second major surface, and wherein the surface portion of the at least one of the sheets is selected from the group of the first major surface, the second major surface, the peripheral surface and combinations thereof.

13. The aircraft windshield according to claim 1, comprising a first moisture sensor, a second moisture sensor, and a third moisture sensor, wherein the first moisture sensor is positioned between the moisture seal and the peripheral edge portion of at least one of the sheets, the second moisture sensor is positioned between the sheets, and the third moisture sensor is positioned between the moisture seal and an outer surface portion of the laminated window.

14. The aircraft windshield according to claim 1, wherein the moisture sensor is a first elongated moisture sensor having a first end and a second opposite end, and comprising second, third, and fourth elongated moisture sensors; each of the moisture sensors comprising a first end and an opposite second end, wherein the first, second, third and fourth moisture sensors are mounted on a major surface of one of a pair of sheets of the plurality of sheets adjacent to peripheral edge portions of the sheet, wherein the second end of the first sensor is adjacent and spaced from the first end of the second sensor, the second end of the second sensor is adjacent and spaced from the first end of the third sensor, the second end of the third sensor is adjacent and spaced from the first end of the fourth sensor, and the second end of the fourth sensor is adjacent and spaced from the first end of the first sensor.

15. The aircraft windshield according to claim 14, wherein the first, second, third and fourth elongated moisture sensors form a first boundary and comprise a second boundary within and spaced from the first boundary, and a third boundary within and spaced from the second boundary, wherein each of the second and third boundaries comprises at least one elongated moisture sensor, defined as a fifth elongated moisture sensor for the second boundary and the sixth elongated moisture sensor for the third boundary.

16. The aircraft windshield according to claim 1, wherein each of the plurality of sheets comprises a first major surface opposite to a second major surface and a peripheral surface joining the first major surface, wherein the second major surface of a first sheet of the plurality of sheets is in facing relationship to and spaced from the second major surface of a second sheet of the plurality of sheets, and wherein the moisture sensor is between the first sheet and the second sheet and spaced from the peripheral surface of the first sheet and the second sheet.

17. The aircraft windshield according to claim 1, wherein one or more of the plurality of sheets of the laminated window is selected from the group of uncured plastic sheets, annealed glass sheets, and heat and chemically strengthened, clear, colored, coated and uncoated glass sheets.

18. The aircraft windshield of claim 1, wherein the power source applies a voltage of known phase and magnitude to the first electrode, and
wherein the electrical measurement mechanism measures the complex impedance of the dielectric material by:
measuring phase and magnitude of voltage of the moisture sensor; and
calculating the complex impedance of the dielectric material based at least in part on a difference between the applied known phase and magnitude and the measured phase and magnitude.

19. A method of making an aircraft transparency having a moisture sensor, comprising:
fabricating a laminated aircraft transparency, the aircraft transparency comprising a plurality sheets joined together to provide a laminated window having a vision area, the window having a moisture seal over an outer surface of marginal edges, and a periphery of the laminated aircraft transparency;
during fabrication of the laminated aircraft transparency placing a sensor element responsive to moisture between the sheets and/or between the sheets and the moisture seal of the laminated aircraft transparency, wherein the sensor element comprises a dielectric material comprising at least one of an extruded sleeve and an extruded layer formed from an absorbent extruded polymer material, between a first electrode and a second electrode of the sensor element, wherein the dielectric material is in electrical contact with the first and second electrodes and maintains the first and the second electrodes spaced from one another and out of contact with one another;
applying alternating electrical current to the electrodes;
measuring a complex impedance (ohms) of the dielectric material; and
determining an amount of moisture within the laminated aircraft transparency in an area of the sensor element.

20. The method of claim 19, wherein applying alternating current to the electrodes to measure the complex impedance (ohms) of the dielectric material, comprises:
applying a voltage of known phase and magnitude to the first electrode;
measuring a phase and magnitude of voltage of the sensor element; and
calculating the complex impedance of the dielectric material based at least in part on a difference between the applied known phase and magnitude and the measured phase and magnitude to determine the amount of moisture within the laminated window in the area of the sensor element.

* * * * *